United States Patent
Jin et al.

(10) Patent No.: US 12,282,016 B2
(45) Date of Patent: Apr. 22, 2025

(54) LABELING METHOD FOR IMPROVING SIGNAL INTENSITY OF TIME-RESOLVED FLUORESCENCE

(71) Applicant: Zhejiang Gongshang University, Hangzhou (CN)

(72) Inventors: Renyao Jin, Hangzhou (CN); Yanling Song, Hangzhou (CN); Xiaoxia Liu, Hangzhou (CN); Jiacheng Yang, Hangzhou (CN); Lu Zhai, Hangzhou (CN)

(73) Assignee: ZHEJIANG GONGSHANG UNIVERSITY, Hangzhou (CN)

( * ) Notice: Subject to any disclaimer, the term of this patent is extended or adjusted under 35 U.S.C. 154(b) by 772 days.

(21) Appl. No.: 17/563,550

(22) Filed: Dec. 28, 2021

(65) Prior Publication Data
US 2022/0412964 A1    Dec. 29, 2022

(30) Foreign Application Priority Data

Jun. 26, 2021 (CN) .......................... 202110715114.4
Jun. 26, 2021 (CN) .......................... 202110715118.2

(51) Int. Cl.
*G01N 33/533* (2006.01)
*G01N 21/64* (2006.01)

(52) U.S. Cl.
CPC ....... *G01N 33/533* (2013.01); *G01N 21/6408* (2013.01); *G01N 21/6428* (2013.01); *G01N 2021/6439* (2013.01)

(58) Field of Classification Search
CPC .......................... G01N 33/533; G01N 32/6408
See application file for complete search history.

(56) References Cited

FOREIGN PATENT DOCUMENTS

| CN | 108264553 A | * | 7/2018 | ........... C07K 14/765 |
| CN | 110927382 A | * | 3/2020 | |
| LU | 500414 B1 | * | 12/2021 | ............. G01N 21/01 |
| WO | WO-2005026730 A2 | * | 3/2005 | ......... G01N 21/6428 |

* cited by examiner

Primary Examiner — Jeffrey T. Palenik
Assistant Examiner — Michael Cameron Sveiven
(74) Attorney, Agent, or Firm — MUNCY, GEISSLER, OLDS & LOWE, P.C.

(57) ABSTRACT

The present invention provides a labeling method for improving signal intensity of time-resolved fluorescence; and the labeling method can be applied in the detection of olaquindox or gentamicin. The olaquindox antibody complex immunolabelled by time-resolved fluorescence prepared in the present invention has a more stable structure, stronger fluorescence signal, and higher detection sensitivity.

2 Claims, 4 Drawing Sheets p-NH$_2$-Bn-NOTA p-NH₂-Bn-NOTA p-NH₂-Bn-DTPA

Aminobenzyl-EDTA p-NH₂-Bn-DOTA

LABELING METHOD FOR IMPROVING SIGNAL INTENSITY OF TIME-RESOLVED FLUORESCENCE

CROSS REFERENCE TO THE RELATED APPLICATIONS

This application claims priority to Chinese Patent Application No. 202110715114.4 filed on Jun. 26, 2021 and Chinese Patent Application No. 202110715118.2 filed on Jun. 26, 2021, the entire contents of which are incorporated herein by reference.

TECHNICAL FIELD

The prevent invention belongs to the technical field of fluorescence immunoassay; and particularly relates to a labeling method for improving signal intensity of time-resolved fluorescence.

BACKGROUND

Time-resolved fluorescence immunoassay (TRFIA) is a kind of booming high-sensitivity detection means in recent years. The principle of TRFIA is to use a chelating agent having a bifunctional group structure, one end thereof is bonded to lanthanide elements, and another end thereof is linked to a free amino group on an antibody (or antigen), thus preparing a lanthanide $Eu^{3+}$-labeled antibody (or antigen) which is bonded to an antigen (or an antibody) in a sample to be tested to generate an antigen-antibody complex. At this time, the immune complex has a very weak fluorescence intensity; thereby it needs to add an enhancement solution, such that $Eu^{3+}$ is dissociated from the complex, and may form a new complex with another chelating agent TTA under the synergistic effect of TOPO, Triton X-100 and the like in the enhancement solution; and the complex may emit very strong fluorescence to enhance million-fold fluorescent effect. Finally, the fluorescence intensity cps thereof is measured by a time resolution meter to determine the content of antigen in the sample.

The intensity of the fluorescence signal of rare earth element fluorescently-labeled antibody complex determines the detection sensitivity and stability of the method to a large extent, and is a key link to build the time-resolved fluorescence immunoassay. At present, the common bifunctional chelating agent used to label $Eu^{3+}$ on an antibody mainly includes derivatives of ethylenediamie tetraacetic acid (EDTA) or diethylene triamine pentaacetic acid (DTPA) and other structural analogs having chelating functions. For example, EDTA and $Eu^{3+}$ ion form a metal-EDTA chelate more stable than the complex. In the prior art, EDTA and DTPA, these conventional chelating agents are open-loop and linear-chain structures; the complex of $Eu^{3+}$ ion and chelating agent has a poor binding stability, which indicates that after being bonded, $Eu^{3+}$ ion is easily dissociated from the complex, and the measured fluorescence signal weakens, and the detection sensitivity and stability will be influenced.

SUMMARY

Directed to the above situation, and to overcome the shortcomings in the prior art, the present application provides a labeling method for improving signal intensity of time-resolved fluorescence.

In one aspect, to achieve the above objective, the prevent disclosure provides the following technical solution:

A labeling method for improving signal intensity of time-resolved fluorescence, includes the following steps:

(1) weighing and dissolving 4-7 mg 2-S-(4-aminobenzene)-1,4,7 triazacyclononane-1,4,7-triacetic acid (p-NH$_2$-Bn-NOTA, abbreviated for NOTA) into a 1 mL 4-hydroxyethylpiperazine ethanesulfonic acid (HEPES) solution (0.01 mol·L$^{-1}$, pH=7.4) to be prepared into an NOTA chelating agent solution, where the solution is a first solution A;

(2) adding a 500-700 µL 20 mmol·L$^{-1}$ glutaraldehyde solution to the solution A for reaction in dark place over the night at room temperature, where the solution is a second solution B;

(3) weighing and dissolving 20-30 mg purified monoclonal antibody lyophilized powder into a 3 ml HEPES solution (0.01 mol·L$^{-1}$, pH=7.4), and performing magnetic stirring for mixing evenly at room temperature, thus obtaining a third solution C;

(4) dropwisely adding the second solution B to the third solution C, then adjusting a pH value to 9.0, and stirring the mixed solution for reaction for 4-6 h in dark place at 4° C., thus obtaining a fourth solution D;

(5) loading the fourth solution D to a dialysis bag having a molecular weight cut-off of 8 KDa for dialysis by an HEPES solution (0.01 mol·L$^{-1}$ pH=7.4), replacing the HEPES solution once every 4 h, and 4-6 times in total, then, absorbing a reaction solution in the dialysis bag to obtain a fifth solution E;

(6) weighing 0.11-0.15 g $EuCl_3 \cdot 6H_2O$, and a $EuCl_3$ solution having a concentration of $3.3 \times 10^{-2}$ mol·L$^{-1}$ with 10 mL ultrapure water, thus obtaining a sixth solution F; and (7) taking and adding 200-400 µL of the sixth solution F to the fifth solution E for reaction for 4-6 h in dark place at room temperature, then placing the solution after reaction to a dialysis bag having a molecular weight cut-off of 8 KDa for dialysis, and replacing the HEPES solution once every 4 h, and 4-5 times in total; centrifuging the dialyzed solution for 3-5 times with a 30 KDa ultrafiltration centrifugal tube at 7000-9000 rpm, and redissolving the remaining solution with a 5-10 ml HEPES solution (0.01 mol·L$^{-1}$, pH=7.4); where the prepared reaction solution is a monoclonal antibody complex immunolabelled by time-resolved fluorescence.

In one embodiment, the monoclonal antibody is an olaquindox monoclonal antibody or a gentamicin monoclonal antibody.

The present disclosure also provides an application of 2-S-(4-aminobenzene)-1,4,7 triazacyclononane-1,4,7-triacetic acid in improving signal intensity of time-resolved fluorescence.

The prevent disclosure has the following beneficial effects:

The olaquindox or gentamicin antibody complex immunolabelled by time-resolved fluorescence prepared in the present invention has a more stable structure, such that the measured fluorescence signal is stronger and the detection sensitivity is higher. The novel bifunctional chelating agent 2-S-(4-aminobenzene)-1,4,7 triazacyclononane-1,4,7-triacetic acid (p-NH$_2$-Bn-NOTA, abbreviated for NOTA) has a feature of triaza closed-loop structure, thereby capable of binding to $Eu^{3+}$ ion better; and the binding site is to wrap $Eu^{3+}$ ions annularly, such that the complex is more stable, has better fluorescence intensity and signal, higher detection sensitivity, and better detection effect.

In another aspect, the disclosure also provides a labeling method for improving signal intensity of time-resolved fluorescence, includes the following steps:

(1) dissolving 5-8 mg 2-S-(4-aminobenzene)-1,4,7,10 tetraazacyclononane-1,4,7,10-tetraacetic acid (P—$NH_2$-Bn-DOTA, abbreviated for DOTA) into a 2 mL 4-hydroxyethylpiperazine ethanesulfonic acid (HEPES) solution (0.01 mol·$L^{-1}$, pH=7.4) to be prepared into a DOTA chelating agent solution, wherein the solution is a first solution A;

(2) adding a 500-70 μL 20 mmol·$L^{-1}$ glutaraldehyde solution to the solution A for reaction in dark place over the night at room temperature, where the solution is a second solution B;

(3) weighing and dissolving 20-30 mg purified monoclonal antibody lyophilized powder into a 3 ml HEPES solution (0.01 mol·$L^{-1}$, pH=7.4), and performing magnetic stirring for mixing evenly at room temperature, thus obtaining a third solution C;

(4) dropwisely adding the second solution B to the third solution C, then adjusting a pH value to 9.0, and stirring the mixed solution for reaction for 4-6 h in dark place at 4° C., thus obtaining a fourth solution D;

(5) loading the fourth solution D to a dialysis bag having a molecular weight cut-off of 8 KDa for dialysis by an HEPES solution (0.01 mol·$L^{-1}$ pH=7.4), replacing the solution for once every 4 h, and 4-6 times in total, then, absorbing a reaction solution in the dialysis bag to obtain a fifth solution E;

(6) weighing 0.11-0.15 g $EuCl_3·6H_2O$, and preparing a $EuCl_3$ solution with 10 mL ultrapure water, thus obtaining a sixth solution F;

(7) taking and adding 200-400 μL of the sixth solution F to the fifth solution E for reaction for 4-6 h in dark place at room temperature, then placing the solution after reaction to a dialysis bag having a molecular weight cut-off of 8 KDa, and replacing the solution for once every 4 h, and 4-5 times in total; centrifuging the dialyzed solution for 3-5 times with a 30 KDa ultrafiltration centrifugal tube at 7000-9000 rpm, and redissolving the remaining solution with a 5-10 ml HEPES solution (0.01 mol·$L^{-1}$, pH=7.4); where the prepared reaction solution is an olaquindox antibody compound immunolabelled by time-resolved fluorescence.

In one embodiment of the other aspect, the monoclonal antibody is an olaquindox monoclonal antibody or a gentamicin monoclonal antibody.

The other aspect also provides an application of 2-S-(4-aminobenzene)-1,4,7,10 tetraazacyclononane-1,4,7,10-tetraacetic acid in improving signal intensity of time-resolved fluorescence.

The other aspect also provides an application of a labeling method for improving signal intensity of time-resolved fluorescence in the detection of olaquindox or gentamicin; and the method is the method mentioned above.

The other aspect has the following beneficial effects:

The olaquindox or gentamicin antibody complex immunolabelled by time-resolved fluorescence prepared in the present invention has a more stable structure, stronger fluorescence signal and a higher detection sensitivity. The novel bifunctional chelating agent 2-S-(4-aminobenzene)-1,4,7,10 tetraazacyclononane-1,4,7,10-tetraacetic acid has a feature of triaza closed-loop structure, thereby capable of binding to $Eu^{3+}$ ion better; and the binding site is to wrap $Eu^{3+}$ ions annularly, such that the complex is more stable, has better fluorescence intensity and signal, higher detection sensitivity, and better detection effect.

DETAILED DESCRIPTION OF THE EMBODIMENTS

Figure 1:
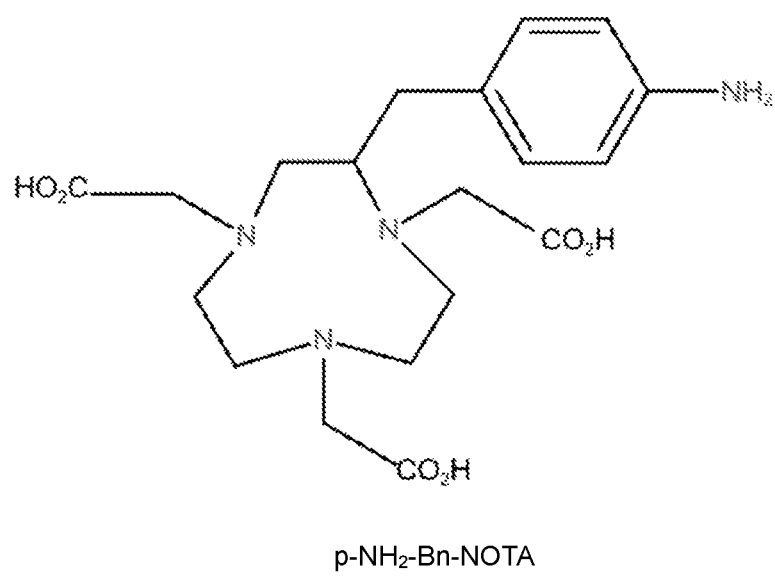
FIG. 1 is a diagram showing a structure of NOTA according to the first embodiment of the disclosure.
Figure 2:
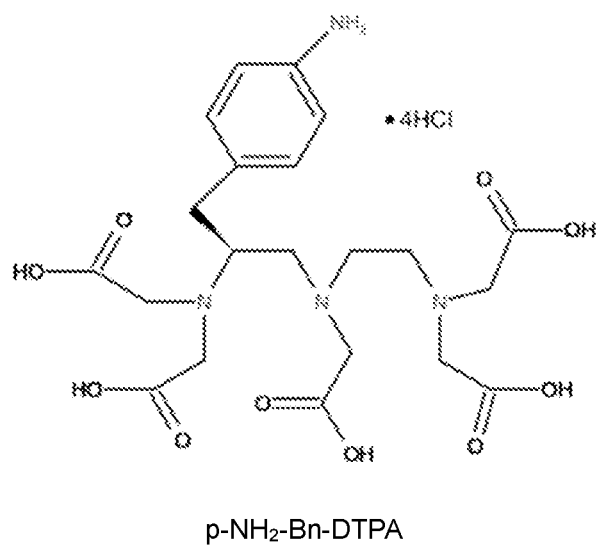
FIG. 2 is a diagram showing a structure of DTPA according to the first or second embodiment of the disclosure.
Figure 3:
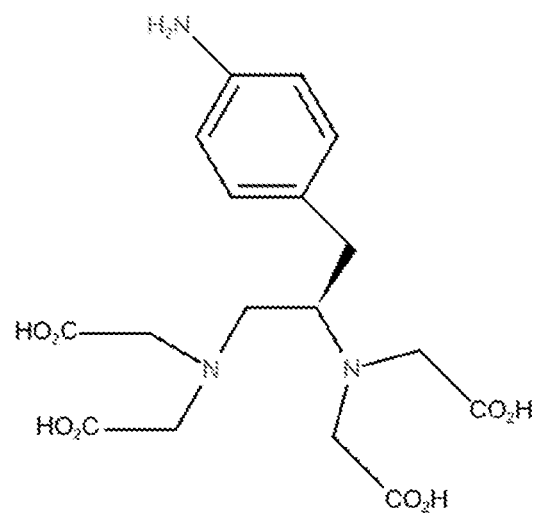
FIG. 3 is a diagram showing a structure of EDTA according to the first or second embodiment of the disclosure.
Figure 4:
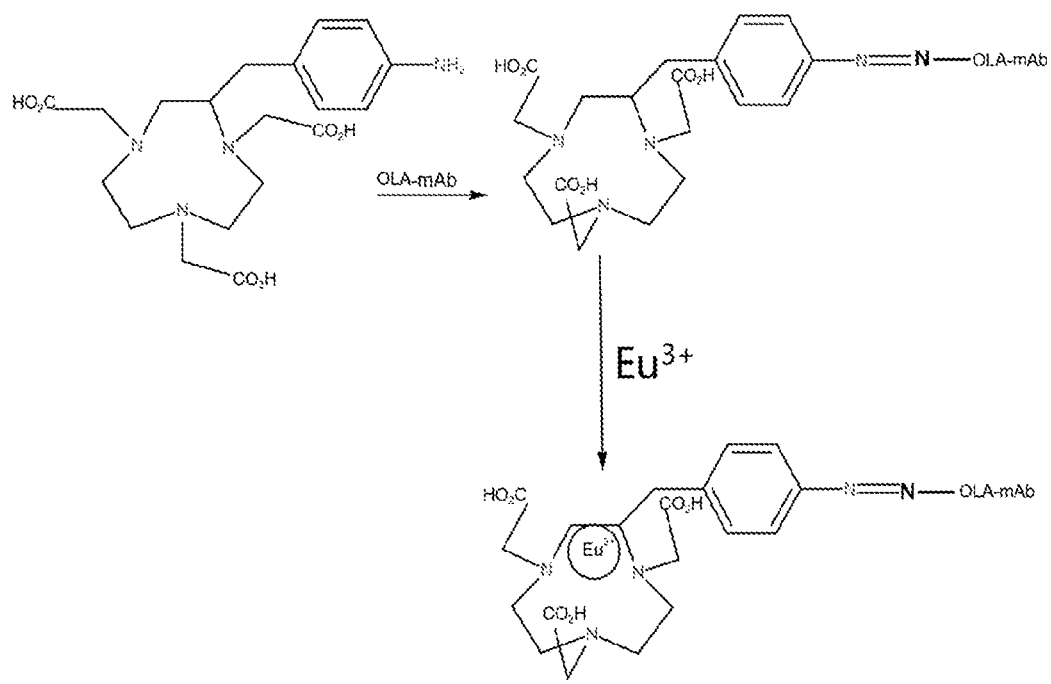
FIG. 4 is a schematic diagram showing a route of preparing an olaquindox antibody-labeled complex according to the first embodiment of the disclosure.
Figure 5:
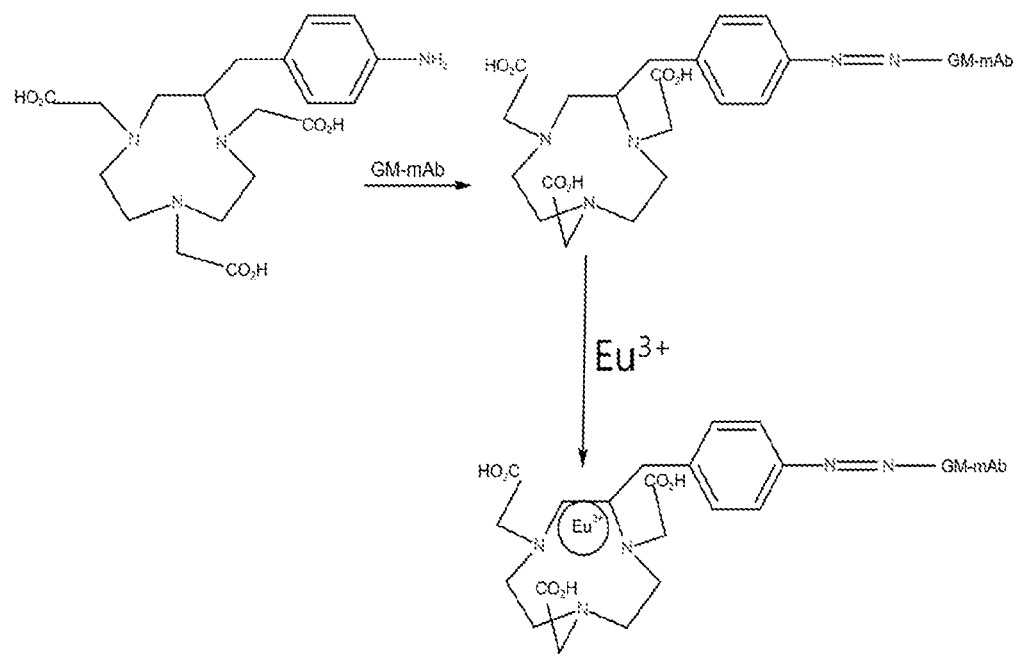
FIG. 5 is a schematic diagram showing a route of preparing a gentamicin antibody-labeled complex according to the first embodiment of the disclosure.
Figure 6:
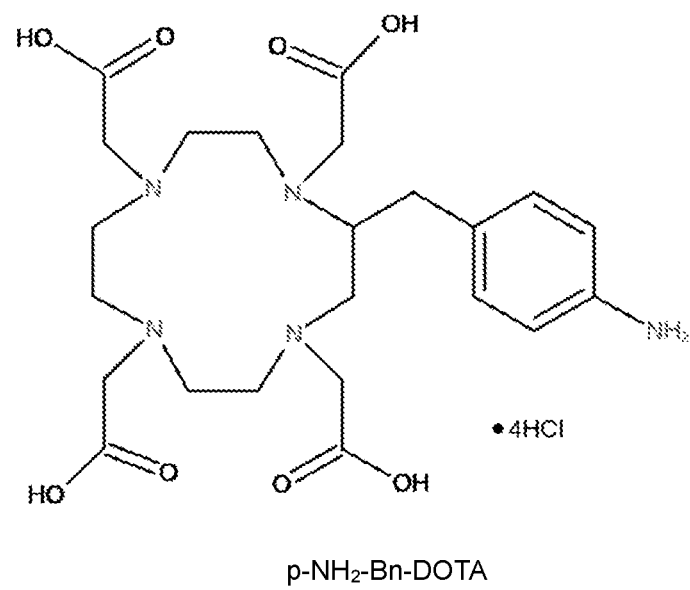
FIG. 6 is a diagram showing a structure of DOTA according to the second embodiment of the disclosure.
Figure 7:
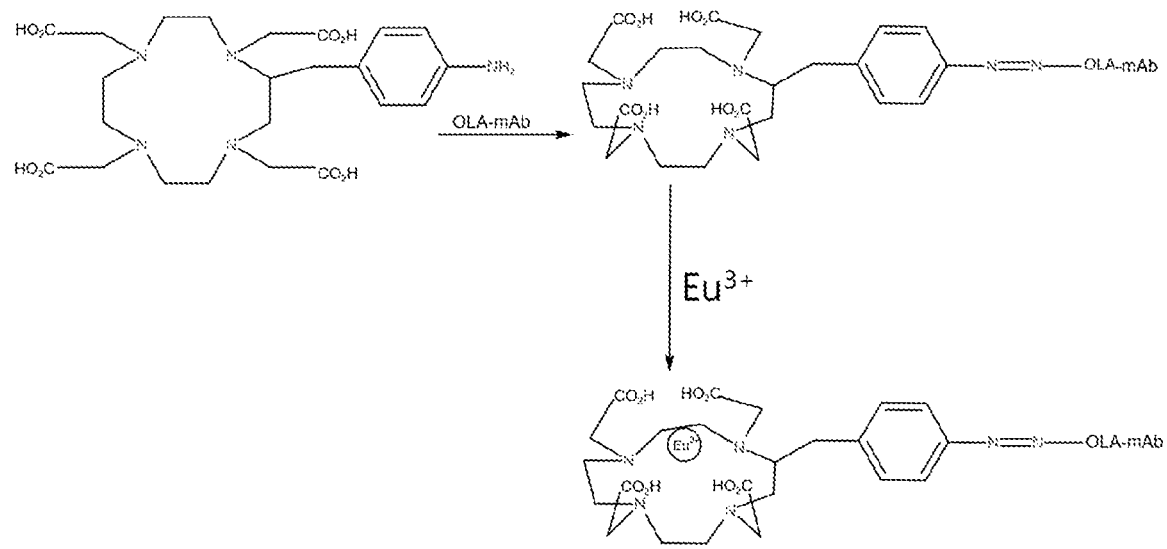
FIG. 7 is a schematic diagram showing a route of preparing an olaquindox antibody-labeled complex according to the second embodiment of the disclosure.
Figure 8:
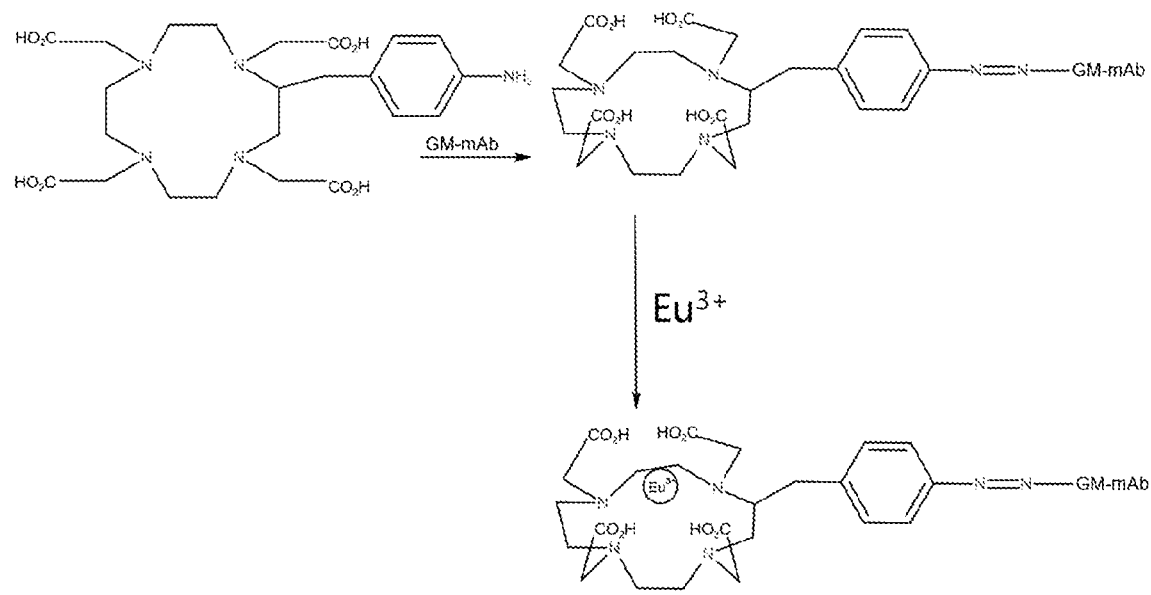
FIG. 8 is a schematic diagram showing a route of preparing a gentamicin antibody-labeled complex according to the second embodiment of the disclosure.

To describe the objective, technical solution and advantages of the present invention more clearly and apparently, the present application will be described and specified in combination with the drawings and examples.

The substances and detecting instrument used in the examples can be purchased by commercial approaches.

The PBS buffer solution used in the examples below, unless otherwise specified, is a 0.01 mol·$L^{-1}$ phosphate buffer solution (pH=7.4); the CBS buffer solution used in the examples is a 0.05 mol·$L^{-1}$ carbonate buffer solution (pH=9.6); bovine serum albumin is abbreviated for BSA; ovalbumin is abbreviated for OVA; keyhole limpet hemocyanin is abbreviated for KLH; olaquindox is abbreviated for OLA, and gentamicin is abbreviated for GM, 1M=1 mol·$L^{-1}$.

First Embodiment

Example 1

A labeling method for improving signal intensity of time-resolved fluorescence, included the following steps: Preparation of an Olaquindox Antibody-Labeled Complex ($Eu^{3+}$-NOTA-OLA-mAb) was Set as an Example for Description:

(1) 6 mg 2-S-(4-aminobenzene)-1,4,7 triazacyclononane-1,4,7-triacetic acid (p-$NH_2$-Bn-NOTA, abbreviated for NOTA) were weighed and dissolved into a 2 mL HEPES solution (0.01 mol·$L^{-1}$, pH=7.4) to be prepared into an NOTA chelating agent solution, where the solution was a solution A;

(2) 520 μL 20 mmol·$L^{-1}$ glutaraldehyde solution was added to the solution A for reaction in dark place over the night at room temperature, where the solution was a solution B;

(3) 20 mg purified olaquindox monoclonal antibody lyophilized powder were weighed and dissolved into a 3 ml HEPES solution (0.01 mol·$L^{-1}$, pH=7.4), and magnetic stirring was performed for mixing evenly at room temperature, thus obtaining a solution C;

in the example, the olaquindox monoclonal antibody (OLA-mAb) was prepared by a conventional method in the prior art (Reference: Yongyu Sang, and Renyao Jin, Development on Anti-Olaquindox Monoclonal Antibodies and Establishment of ELISA Method Thereof, Journal of Nuclear Agricultural Sciences, 2015, 29 (6):1081-1087). Ascitic fluid was purified by an octanoic acid-ammonium sulfate process, and then purified by passing a protein A affinity column, and lyophilized to obtain an OLA-mAb lyophilized powder.

(4) the solution B was dropwisely added to the solution C, then a pH value was adjusted to 9.0, and the mixed solution was stirred for reaction for 6 h in dark place at 4° C., thus obtaining a solution D;

(5) the solution D was loaded to a dialysis bag having a molecular weight cut-off of 8 KDa for dialysis by an HEPES solution (0.01 mol·L$^{-1}$ pH=7.4), the solution was replaced for once every 4 h, and 4-5 times in total, then, a reaction solution in the dialysis bag was absorbed to obtain a solution E;

(6) 0.121 g EuCl$_3$·6H$_2$O was weighed and prepared into a EuCl$_3$ solution having a concentration of 3.3×10$^{-2}$ mol·L$^{-1}$ with 10 mL ultrapure water, thus obtaining a solution F;

(7) 200 μL solution F was taken and added to the solution E for reaction for 4-6 h in dark place at room temperature, then the solution after reaction was placed to a dialysis bag having a molecular weight cut-off of 8 KDa, and the solution was replaced for once every 4 h during dialysis, and 4-5 times in total; the dialyzed solution was centrifuged for 3-5 times with a 30 KDa ultrafiltration centrifugal tube at 7000-9000 rpm, and the remaining solution was redissolved with a 5-10 ml HEPES solution (0.01 mol·L$^{-1}$, pH=7.4); where the prepared reaction solution was an olaquindox antibody complex immunolabelled by time-resolved fluorescence.

Eu$^{3+}$ content was measured by an Inductively Coupled Plasma-Atomic Emission Spectrometry (ICP-AES); a BCA protein concentration assay kit was used to measure the protein concentration in conjugates, then the protein concentration was converted into a molar concentration, and a binding ratio was calculated to 23:1, indicating a ratio of quantity; protein molecule: Eu$^{3+}$=1:23. The results indicated that the NOTA chelating agent was respectively bonded to olaquindox monoclonal antibody and Eu$^{3+}$ to successfully prepare an olaquindox antibody-labeled complex (Eu$^{3+}$-NOTA-OLA-mAb).

Verification of the Preparation Effect:

It was measured by olaquindox TRFIA, and specific steps were as follows:

a. coating: a coating antigen (OLA-HS-OVA) was diluted by CBS (0.05 mol·L$^{-1}$, pH=9.6) to a concentration of 5 μg·mL$^{-1}$, and coated on a 96-well plate with 100 μL per well, and incubated for 2 h at 37° C. in a constant temperature and humidity incubator, then the well plate was washed by a plate washing machine for 4 times, and pat-dried (the same below);

b. blocking: 300 μL 2% (m/v) skimmed milk prepared by PBS (0.01 mol·L$^{-1}$, pH=7.4) was added per well for incubation for 30 min at 37° C., then the well plate was washed for 4 times and pat-dried;

c. adding olaquindox standard samples and Eu$^{3+}$-NOTA-OLA-mAb labels: OLA standard substances having concentrations of the standard series were added to wells, 50 μL per well; then a europium-labeled antibody (Eu$^{3+}$-NOTA-OLA-mAb) was diluted to 2.5 μg·mL$^{-1}$, and added to wells, 50 μL per well; after being oscillated for 30 s, the well plate was put to a 37° C. incubator for incubation for 1 h, and the plate was washed for 4 times and pat-dried;

d. adding an enhancement solution: 200 μL enhancement solution was added per well for oscillatory reaction for 10 min in dark place at 37° C., and detected by a time-resolved fluorescence analyzer;

e. reading and analysis: values (CPS) of the fluorometer were read to establish a standard curve and calculate IC$_{50}$ values and IC$_{10}$ values.

Preparation of Various Reagents:

A. Olaquindox standard solution having concentrations of the standard series: the concentrations were successively 0 ng·mL$^{-1}$, 0.01 ng·mL$^{-1}$, 0.05 ng·mL$^{-1}$, 0.1 ng·mL$^{-1}$, 0.5 ng·mL$^{-1}$, 1.0 ng·mL$^{-1}$, 2.0 ng·mL$^{-1}$, 4.0 ng·mL$^{-1}$, 8.0 ng·mL$^{-1}$, 16.0 ng·mL$^{-1}$, and 32 ng·mL$^{-1}$, and obtained by diluting pure OLA; and the diluent was a 0.01 mol·L$^{-1}$ phosphate buffer solution (pH=7.4) containing 5% (v/v) methanol.

B. Coating a buffer solution CBS: namely, a 0.05 mol·L$^{-1}$ carbonate buffer solution (pH=9.6); 1.49 g Na$_2$CO$_3$ and 2.93 g NaHCO$_3$ were weighed and adjusted to pH=9.6, and metered to a volume of 1000 mL with ultrapure water.

C. Blocking solution: namely, a 0.01 mol·L$^{-1}$ phosphate buffer solution (PBS) (pH=7.4) containing 2% (m/v, g/mL) skimmed milk powder.

D. Cleaning solution: namely, a 0.01 mol·L$^{-1}$ phosphate buffer solution (PBS) (pH=7.4) containing 0.05% (a volume fraction) Tween-20.

E. Diluent: namely, a 0.01 mol·L$^{-1}$ phosphate buffer solution (PBS) (pH=7.4) containing 5% (a volume fraction) methanol.

F. Enhancement solution: 120.0 mg a-thenoyltrifluoroacetone (TTA) and 386.6 mg trioctylphosphine oxide (TOPO) were accurately weighed and dissolved by adding 1.0 mL absolute ethyl alcohol, then 2.78 g potassium hydrogen phthalate and a small amount of deionized water were added, after dissolving at 40° C., 11.8 mL glacial acetic acid and 5 mL Triton X-100 were added, and finally metered to a volume of 2000 mL with water. The pH value was adjusted to 3.0, suction filtration was performed with degreasing cotton, and filtrate was standing over the night, and kept in dark place via a 4° C. refrigerator for further use.

G: Preparation of OLA-HS-OVA: a conventional method in the prior art was used for preparation available, and specifically as follows, 2.106 g olaquindox and 1.60 g succinic anhydride were accurately added to a three-necked round-bottom flask, and 80 mL pyridine was added for reflux reaction for 4 h at 115° C., the pyridine was removed by evaporation under reduced pressure, 60 mL icy distilled water was added to the remaining mixture, and a pH value was adjusted to 2.0-3.0 by 2 mol·L$^{-1}$ HCl, then the remaining solution stayed over the night at 4° C. Afterwards, the remaining solution was subjected to suction filtration under reduced pressure, and washed by icy distilled water for 3 times, and dried by suction, and the obtained substance was OLA-HS;

14.5 mg OLA-HS were weighed and dissolved into 0.8 ml DMF, and 4.6 mg NHS and 8.2 mg DCC were added for stirring reaction for 10 h in dark place at room temperature. The reaction solution was centrifuged (2000 rpm, 10 min), precipitate was discarded and supernate was a reaction solution a.

20 mg OVA were weighed and dissolved into a 5 ml phosphate buffer solution (PBS, 0.01 mol·L$^{-1}$, PH=7.4) to obtain a reaction solution b. The reaction solution b was put on a magnetic stirrer; 0.6 ml reaction solution a was slowly added to the reaction solution b dropwisely at 4° C., and stirred for reaction over the night at 4° C. In the following day, the reaction solution was put to a dialysis bag for dialysis for 4-5 times per day with a phosphate buffer solution (0.01 mol·L$^{-1}$, pH=7.4), then dialyzed for 12 h by ultrapure water, and centrifuged; precipitate was discarded and supernate was subpackaged to obtain OLA-HS-OVA, and OLA-HS-OVA was kept at −20° C. for further use.

Example 2

A labeling method for improving signal intensity of time-resolved fluorescence, included the following steps: Preparation of a Gentamicin Antibody-Labeled Complex (Eu$^{3+}$-NOTA-GM-mAb) was Set as an Example for Description:

(1) 5.5 mg 2-S-(4-aminobenzene)-1,4,7 triazacyclo-nonane-1,4,7-triacetic acid (p-NH$_2$-Bn-NOTA, abbreviated for NOTA) were weighed and dissolved into a 2 mL HEPES solution (0.01 mol·L$^{-1}$, pH=7.4) to be prepared into an NOTA chelating agent solution, where the solution was a solution A;

(2) 520 μL 20 mmol·L$^{-1}$ glutaraldehyde solution was added to the solution A for reaction in dark place over the night at room temperature, where the solution was a solution B;

(3) 20 mg purified GM-mAb lyophilized powder were weighed and dissolved into a 3 ml HEPES solution (0.01 mol·L$^{-1}$, pH=7.4), and magnetic stirring was performed for mixing evenly at room temperature, thus obtaining a solution C;

GM-mAb was prepared by a conventional method in the prior art (Reference: Renyao Jin, and Jianxiang Wu; Development on Gentamicin Monoclonal Antibodies and Establishment of ELISA Method Thereof, Journal of Nuclear Agricultural Sciences, 2013, 27 (1):88-92). After ascitic fluid was prepared, and roughly purified by octanoic acid-ammonium sulfate, and then purified by a Protein A affinity column, and lyophilized to obtain a GM-mAb lyophilized powder.

(4) the solution B was dropwisely added to the solution C, then a pH value was adjusted by NaOH to 9.0, and the mixed solution was stirred for reaction for 4-6 h in dark place at 4° C., thus obtaining a solution D;

(5) the solution D was loaded to a dialysis bag having a molecular weight cut-off of 8 KDa for dialysis by an HEPES solution (0.01 mol·L$^{-1}$ pH=7.4), the solution was replaced for once every 4 h, and 4-5 times in total, then, a reaction solution was absorbed in the dialysis bag to obtain a solution E;

(6) 0.121 g EuCl$_3$.6H$_2$O was weighed and prepared into a EuCl$_3$ solution having a concentration of 3.3×10$^{-2}$ mol·L$^{-1}$ with 10 mL ultrapure water, thus obtaining a solution F;

(7) 250 μL solution F was taken and added to the solution E for reaction for 4-6 h in dark place at room temperature, then the solution after reaction was placed to a dialysis bag having a molecular weight cut-off of 8 KDa for dialysis by an HEPES (0.01 mol·L$^{-1}$, pH=7.4) solution; and the solution was replaced for once every 4 h during dialysis, and 4-5 times in total; the dialyzed solution was centrifuged for 3-5 times with a 30 KDa ultrafiltration centrifugal tube at 7000-9000 rpm, and the remaining solution was redissolved with a 5-10 ml HEPES solution (0.01 mol·L$^{-1}$, pH=7.4); where the prepared reaction solution was a gentamicin antibody-labeled complex.

Eu$^{3+}$ content was measured by an Inductively Coupled Plasma-Atomic Emission Spectrometry (ICP-AES); a BCA protein concentration assay kit was used to measure the protein concentration in conjugates, then the protein concentration was converted into a molar concentration, and a binding ratio was calculated to 19:1, indicating a ratio of quantity; protein molecule: Eu$^{3+}$=1:19. The results indicated that the NOTA chelating agent was respectively bonded to gentamicin monoclonal antibody and Eu$^{3+}$ to successfully prepare a gentamicin antibody-labeled complex (Eu$^{3+}$-NOTA-GM-mAb).

Effect Detection

It was measured by gentamicin TRFIA, and specific steps were as follows:

a. coating: a coating antigen (GM-OVA) was diluted by CBS (0.05 mol·L$^{-1}$, pH=9.6) to a concentration of 5 μg·mL$^{-1}$, and coated on a 96-well plate with 100 μL per well, and incubated for 2 h at 37° C. in a constant temperature incubator, then the well plate was washed by a plate washing machine for 4 times, and pat-dried (the same below);

b. blocking: 300 μL 2% (m/v) skimmed milk prepared by PBS (0.01 mol·L$^{-1}$, pH=7.4) was added per well for incubation for 30 min at 37° C., then the well plate was washed for 4 times and pat-dried;

c. adding gentamicin standard samples and Eu$^{3+}$-NOTA-GM-mAb labels: gentamicin standard substances having concentrations of the standard series were added to wells, 50 μL per well; then an europium-labeled antibody (Eu$^{3+}$-NOTA-GM-mAb) was diluted to 2.5 μg·mL$^{-1}$, and added to wells, 50 μL per well; after being oscillated for 30 s, the well plate was put to a 37° C. incubator for incubation for 1 h, and the plate was washed for 4 times and pat-dried;

d. adding an enhancement solution: 200 μL enhancement solution was added per well for oscillatory reaction for 10 min in dark place at 37° C.

e. reading and analysis: values (CPS) of the fluorometer were read to establish a standard curve and calculate IC$_{50}$ values and IC$_{10}$ values.

Preparation of Various Reagents:

A. Gentamicin standard solution having concentrations of the standard series: the concentrations were successively 0 ng·mL$^{-1}$, 1 ng·mL$^{-1}$, 2 ng·mL$^{-1}$, 4 ng·mL$^{-1}$, 0.5 ng·mL$^{-1}$, 8 ng·mL$^{-1}$, 16 ng·mL$^{-1}$, 32 ng·mL$^{-1}$, 64 ng·mL$^{-1}$, and 128 ng·mL$^{-1}$, and obtained by diluting pure gentamicin; and the diluent is a 0.01 mol·L−1 phosphate buffer solution (pH=7.4).

B. Coating buffer solution: namely, a 0.05 mol·L$^{-1}$ carbonate buffer solution (pH=9.6); 1.49 g Na$_2$CO$_3$ and 2.93 g NaHCO$_3$ were weighed and adjusted to pH=9.6, and metered to a volume of 1000 mL with ultrapure water.

C. Blocking solution: namely, a 0.01 mol·L$^{-1}$ phosphate buffer solution (PBS) (pH=7.4) containing 2% (m/v, g$^{-1}$) skimmed milk powder.

D. Cleaning solution: namely, a 0.01 mol·L$^{-1}$ phosphate buffer solution (PBS) (pH=7.4) containing Tween-20 (volume fraction was 0.05%).

E. Diluent: namely, a 0.01 mol·L$^{-1}$ phosphate buffer solution (PBS) (pH=7.4).

F. Enhancement solution: 120.0 mg a-thenoyltrifluoroacetone (TTA) and 386.6 mg trioctylphosphine oxide (TOPO) were weighed and dissolved by adding 1.0 mL absolute ethyl alcohol, then 2.78 g potassium hydrogen phthalate and a small amount of deionized water were added, after dissolving at 40° C., 11.8 mL glacial acetic acid and 5 mL Triton X-100 were added, and finally metered to a volume of 2000 mL with water. The pH value was adjusted to 3.0, suction filtration was performed with degreasing cotton, and filtrate was standing over the night, and kept in dark place via a 4° C. refrigerator for further use.

G: Synthesis of GM-OVA: a conventional method in the prior art was used for preparation available, and specifically as follows, 20 mg GM and 12 mg OVA were taken, and respectively dissolved by 1 ml ultrapure water; then GM solution was dropwisely added to OVA solution while stirring slowly; 62 mg carbodiimide (EDC) were weighed and dissolved into 1 ml ultrapure water, then the above mixed solution was added dropwisely, and stirred for reaction for 4 h at room temperature; afterwards, the reaction product was loaded to a dialysis bag for dialysis for 2 d, and the solution was replaced for once every 4 h, after replacing for 4-5 times, the remaining solution was subpackaged, and kept at −20° C.

Comparative Example 1

Preparation of an Olaquindox Fluorescent Antibody Complex ($Eu^{3+}$-EDTA-OLA-mAb):

(1) 5.5 mg EDTA was weighed and dissolved into a 1 mL 4-hydroxyethylpiperazine ethanesulfonic acid (HEPES) solution (0.01 mol·$L^{-1}$, pH=7.4) to be prepared into an EDTA chelating agent solution, where the solution was a solution A;

(2) 520 μL 20 mmol·$L^{-1}$ glutaraldehyde solution was added to the solution A for reaction in dark place over the night at room temperature, where the solution was a solution B;

(3) 20 mg purified OLA-mAb lyophilized powder were weighed and dissolved into a 3 ml HEPES solution (0.01 mol·$L^{-1}$, pH=7.4), and magnetic stirring was performed for mixing evenly at room temperature, thus obtaining a solution C; and the preparation method of the OLA-mAb lyophilized powder was the same as that in Example 1;

(4) the solution B was dropwisely added to the solution C, then a pH value was adjusted by NaOH to 9.0, and the mixed solution was stirred for reaction for 4-6 h in dark place at 4° C., thus obtaining a solution D;

(5) the solution D was loaded to a dialysis bag having a molecular weight cut-off of 8 KDa for dialysis by an HEPES solution (0.01 mol·$L^{-1}$ pH=7.4), the solution was replaced for once every 4 h, and 4-5 times in total, then, a reaction solution was absorbed in the dialysis bag to obtain a solution E;

(6) 0.121 g $EuCl_3·6H_2O$ was weighed and prepared into a $EuCl_3$ solution having a concentration of $3.3×10^{-2}$ mol·$L^{-1}$ with 10 mL ultrapure water, thus obtaining a solution F;

(7) 200 μL solution F was taken and added to the solution E for reaction for 4-6 h in dark place at room temperature, then the solution after reaction was placed to a dialysis bag having a molecular weight cut-off of 8000 Da for dialysis by an HEPES (0.01 mol·$L^{-1}$, pH=7.4) solution; and the solution was replaced for once every 4 h during dialysis, and 4-5 times in total; the dialyzed solution was centrifuged for 3-5 times with a 30 KDa ultrafiltration centrifugal tube at 7000-9000 rpm, and the remaining solution was redissolved with a 5-10 ml HEPES solution (0.01 mol·$L^{-1}$, pH=7.4); where the prepared reaction solution was an olaquindox antibody complex immunolabelled by time-resolved fluorescence.

$Eu^{3+}$ content was measured by an Inductively Coupled Plasma-Atomic Emission Spectrometry (ICP-AES); a BCA protein concentration assay kit was used to measure the protein concentration in conjugates, then the protein concentration was converted into a molar concentration, and a binding ratio was calculated to 10:1, indicating a ratio of quantity; protein molecule: $Eu^{3+}$=1:10. The results indicated that EDTA was respectively bonded to olaquindox monoclonal antibody and $Eu^{3+}$ to successfully prepare an olaquindox antibody-labeled complex.

Verification of the preparation effect: it was measured by olaquindox TRFIA, and specific steps were as follows:

a. coating: a coating antigen (OLA-HS-OVA) was diluted by CBS (0.05 mol·$L^{-1}$, pH=9.6) to a concentration of 5 μg·$mL^{-1}$, and coated on a 96-well plate with 100 μL per well, and incubated for 2 h at 37° C. in a constant temperature and humidity incubator, then the well plate was washed by a plate washing machine for 4 times, and pat-dried (the same below);

b. blocking: 300 μL 2% skimmed milk prepared by PBS (0.01 mol·$L^{-1}$, pH=7.4) was added per well for incubation for 30 min at 37° C., then the well plate was washed;

c. olaquindox standard samples and $Eu^{3+}$-EDTA-OLA-mAb labels: OLA standard substances having concentrations of the standard series were added to wells, 50 μL per well; then an europium-labeled antibody ($Eu^{3+}$-EDTA-OLA-mAb) was diluted to 2.5 μg·$mL^{-1}$, and added to wells, 50 μL per well; after being oscillated for 30 s, the well plate was put to a 37° C. incubator for incubation for 1 h, and the plate was washed;

d. adding an enhancement solution: 200 μL enhancement solution was added per well for oscillatory reaction for 10 min in dark place at 37° C.;

e. reading and analysis: values (CPS) of the fluorometer were read to establish a standard curve and calculate $IC_{50}$ values and $IC_{10}$ values.

Comparative Example 2

Preparation of an Olaquindox Antibody-Labeled Complex ($Eu^{3+}$-DTPA-OLA-mAb):

(1) 5.5 mg p-$NH_2$-Bn-DTPA (hereinafter referred to as DTPA) were weighed and dissolved into a 2 ml HEPES buffer solution (0.01 mol·$L^{-1}$, pH=7.4) to be prepared into a DTPA chelating agent solution, where the reaction solution was a solution A;

(2) 520 μL 20 mmol·$L^{-1}$ glutaraldehyde solution was added to the solution A for reaction in dark place over the night at room temperature, where the solution was a solution B;

(3) 20 mg purified OLA-mAb lyophilized powder were weighed and dissolved into a 3 ml HEPES solution (0.01 mol·$L^{-1}$, pH=7.4), and magnetic stirring was performed for mixing evenly at room temperature, thus obtaining a solution C; and the preparation method of the OLA-mAb lyophilized powder was the same as that in Example 1.

The solution B was dropwisely added to the solution C, then a pH value was adjusted by NaOH to 9.0, and the mixed solution was stirred for reaction for 4-6 h in dark place at 4° C., thus obtaining a solution D;

(4) the solution D was loaded to a dialysis bag having a molecular weight cut-off of 8 KDa for dialysis by an HEPES solution (0.01 mol·L$^{-1}$ pH=7.4), the solution was replaced for once every 4 h, and 4-5 times in total, then, a reaction solution was absorbed in the dialysis bag to obtain a solution E;

(5) 0.121 g EuCl$_3$.6H$_2$O was weighed and prepared into a EuCl$_3$ solution having a concentration of 3.3×10$^{-2}$ mol·L$^{-1}$ with 10 mL ultrapure water, thus obtaining a solution F;

(6) 200 μL solution F was taken and added to the solution E for reaction for 4-6 h in dark place at room temperature, then the solution after reaction was placed to a dialysis bag having a molecular weight cut-off of 8 KDa for dialysis by an HEPES (0.01 mol·L$^{-1}$, pH=7.4) solution; and the solution was replaced for once every 4 h during dialysis, and 4-5 times in total; the dialyzed solution was centrifuged for 3-5 times with a 30 KDa ultrafiltration centrifugal tube at 7000-9000 rpm, and the remaining solution was redissolved with a 5-10 ml HEPES solution (0.01 mol·L$^{-1}$, pH=7.4); where the prepared reaction solution was an olaquindox antibody complex immunolabelled by time-resolved fluorescence.

Eu$^{3+}$ content was measured by an Inductively Coupled Plasma-Atomic Emission Spectrometry (ICP-AES); a BCA protein concentration assay kit was used to measure the protein concentration in conjugates, then the protein concentration was converted into a molar concentration, and a binding ratio was calculated to 8:1, indicating a ratio of quantity; protein molecule: Eu$^{3+}$=1:8. The results indicated that DTPA was respectively bonded to olaquindox monoclonal antibody and Eu$^{3+}$ to successfully prepare an olaquindox antibody-labeled complex (Eu$^{3+}$-DTPA-OLA-mAb).

Effect Detection:

It was measured by Olaquindox TRFIA, and specific steps were as follows:

a. coating: a coating antigen (OLA-HS-OVA) was diluted by CBS (0.05 mol·L$^{-1}$, pH=9.6) to a concentration of 5 μg·mL$^{-1}$, and coated on a 96-well plate with 100 μL per well, and incubated for 2 h at 37° C. in a constant temperature incubator, then the well plate was washed by a plate washing machine for 4 times, and pat-dried (the same below);

b. blocking: 300 μL 2% (m/v) skimmed milk prepared by PBS (0.01 mol·L$^{-1}$, pH=7.4) was added per well for incubation for 30 min at 37° C., then the well plate was washed for 4 times and pat-dried;

c. adding olaquindox standard samples and Eu$^{3+}$-DTPA-OLA-mAb labels: OLA standard solution having concentrations of the standard series was added to wells, 50 μL per well; then an europium-labeled antibody (Eu$^{3+}$-DTPA-OLA-mAb) was diluted to 2.5 μg·mL$^{-1}$, and added to wells, 50 μL per well; after being oscillated for 30 s, the well plate was put to a 37° C. incubator for incubation for 1 h, and the plate was washed for 4 times and pat-dried;

d. adding an enhancement solution: 200 μL enhancement solution was added per well for oscillatory reaction for 10 min in dark place at 37° C., and detected by a time-resolved fluorescence analyzer;

e. reading and analysis: values (CPS) of the fluorometer were read to establish a standard curve and calculate IC$_{50}$ values and IC$_{10}$ values.

Comparative Example 3

Preparation of a Gentamicin Antibody-Labeled Complex (Eu$^{3+}$-EDTA-GM-mAb):

(1) 5.5 mg Aminobenzy-EDTA (hereinafter referred to as EDTA) were weighed and dissolved into a 2 ml HEPES buffer solution (0.01 mol·L$^{-1}$, pH=7.4) to be prepared into an EDTA chelating agent solution, where the reaction solution was a solution A;

(2) 520 μL 20 mmol·L$^{-1}$ glutaraldehyde solution was added to the solution A for reaction in dark place over the night at room temperature, where the solution was a solution B;

(3) 20 mg purified GM-mAb lyophilized powder were weighed and dissolved into a 3 ml HEPES solution (0.01 mol·L$^{-1}$, pH=7.4), and magnetic stirring was performed for mixing evenly at room temperature, thus obtaining a solution C; and the preparation method of the GM-mAb lyophilized powder was the same as that in Example 2.

(4) the solution B was dropwisely added to the solution C, then a pH value was adjusted by NaOH to 9.0, and the mixed solution was stirred for reaction for 4-6 h in dark place at 4° C., thus obtaining a solution D;

(5) the solution D was loaded to a dialysis bag having a molecular weight cut-off of 8 KDa for dialysis by an HEPES solution (0.01 mol·L$^{-1}$ pH=7.4), the solution was replaced for once every 4 h, and 5-6 times in total, then, a reaction solution was absorbed in the dialysis bag to obtain a solution E;

(6) 0.121 g EuCl$_3$.6H$_2$O was weighed and prepared into a EuCl$_3$ solution having a concentration of 3.3×10$^{-2}$ mol·L$^{-1}$ with 10 mL ultrapure water, thus obtaining a solution F;

(7) 250 μL solution F was taken and added to the solution E for reaction for 4-6 h in dark place at room temperature, then the solution after reaction was placed to a dialysis bag having a molecular weight cut-off of 8 KDa for dialysis by an HEPES (0.01 mol·L$^{-1}$, pH=7.4) solution; and the solution was replaced during dialysis for once every 4 h, and 4-5 times in total; the dialyzed solution was centrifuged for 3-5 times with a 30 KDa ultrafiltration centrifugal tube at 7000-9000 rpm, and the remaining solution was redissolved with a 5-10 ml HEPES solution (0.01 mol·L$^{-1}$, pH=7.4); where the prepared reaction solution was a gentamicin antibody-labeled complex.

Eu$^{3+}$ content was measured by an Inductively Coupled Plasma-Atomic Emission Spectrometry (ICP-AES); a BCA protein concentration assay kit was used to measure the protein concentration in conjugates, then the protein concentration was converted into a molar concentration, and a binding ratio was calculated to 7:1, indicating a ratio of quantity; protein molecule: Eu$^{3+}$=1:7. The results indicated that EDTA was respectively bonded to gentamicin monoclonal antibody and Eu$^{3+}$ to successfully prepare a gentamicin antibody-labeled complex (Eu$^{3+}$-EDTA-GM-mAb).

Effect Detection

It was measured by gentamicin TRFIA, and specific steps were as follows:

a. coating: a coating antigen (GM-OVA) was diluted by CBS (0.05 mol·L$^{-1}$, pH=9.6) to a concentration of 5 μg·mL$^{-1}$, and coated on a 96-well plate with 100 μL per well, and incubated for 2 h at 37° C. in a constant temperature incubator, then the well plate was washed by a plate washing machine for 4 times, and pat-dried (the same below).

b. blocking: 300 μL 2% (m/v) skimmed milk prepared by PBS (0.01 mol·L$^{-1}$, pH=7.4) was added per well for incubation for 30 min at 37° C., then the well plate was washed for 4 times and pat-dried;

c. adding gentamicin standard samples and Eu$^{3+}$-EDTA-GM-mAb labels: gentamicin standard substances having a concentration of the standard series were added to wells, 50 μL per well; then an europium-labeled antibody (Eu$^{3+}$-EDTA-GM-mAb) was diluted to 2 μg·mL$^{-1}$, and added to wells, 50 μL per well; after being oscillated for 30 s, the well plate was put to a 37° C. incubator for incubation for 1 h, and the plate was washed for 4 times and pat-dried;

d. adding an enhancement solution: 200 μL enhancement solution was added per well for oscillatory reaction for 10 min in dark place at 37° C.

e. reading and analysis: values (CPS) of the fluorometer were read to establish a standard curve and calculate IC$_{50}$ values and IC$_0$ values.

Comparative Example 4

Preparation of a Gentamicin Antibody-Labeled Complex (Eu$^{3+}$-DTPA-GM-mAb):

(1) 5.5 mg p-NH$_2$-Bn-DTPA were weighed and dissolved into a 2 ml HEPES buffer solution (0.01 mol·L$^{-1}$, pH=7.4) to be prepared into a DTPA chelating agent solution, where the reaction solution was a solution A;

(2) 520 μL 20 mmol·L$^{-1}$ glutaraldehyde solution was added to the solution A for reaction in dark place over the night at room temperature, where the solution was a solution B;

(3) 20 mg purified GM-mAb lyophilized powder were weighed and dissolved into a 3 ml HEPES solution (0.01 mol·L$^{-1}$, pH=7.4), and magnetic stirring was performed for mixing evenly at room temperature, thus obtaining a solution C; and the preparation method of the GM-mAb lyophilized powder was the same as that in Example 2.

(4) the solution B was dropwisely added to the solution C, then a pH value was adjusted by NaOH to 9.0, and the mixed solution was stirred for reaction for 4-6 h in dark place at 4° C., thus obtaining a solution D;

(5) the solution D was loaded to a dialysis bag having a molecular weight cut-off of 8 KDa for dialysis by an HEPES solution (0.01 mol·L$^{-1}$ pH=7.4), the solution was replaced for once every 4 h, and 5 times in total, then, a reaction solution in the dialysis bag was absorbed to obtain a solution E;

(6) 0.121 g EuCl$_3$.6H$_2$O was weighed and prepared into a EuCl$_3$ solution having a concentration of 3.3×10$^{-2}$ mol·L$^{-1}$ with 10 mL ultrapure water, thus obtaining a solution F;

(7) 250 μL solution F was taken and added to the solution E for reaction for 4-6 h in dark place at room temperature, then the solution after reaction was placed to a dialysis bag having a molecular weight cut-off of 8 KDa for dialysis by an HEPES (0.01 mol·L$^{-1}$, pH=7.4) solution; and the solution was replaced for once every 4 h during dialysis, and 4-5 times in total; the dialyzed solution was centrifuged for 3-5 times with a 30 KDa ultrafiltration centrifugal tube at 7000-9000 rpm, and the remaining solution was redissolved with a 5-10 ml HEPES solution (0.01 mol·L$^{-1}$, pH=7.4); where the prepared reaction solution was a gentamicin antibody-labeled complex.

Eu$^{3+}$ content was measured by an Inductively Coupled Plasma-Atomic Emission Spectrometry (ICP-AES); a BCA protein concentration assay kit was used to measure the protein concentration in conjugates, then the protein concentration was converted into a molar concentration, and a binding ratio was calculated to 9:1, indicating a ratio of quantity; protein molecule: Eu$^{3+}$=1:9. The results indicated that DTPA was respectively bonded to gentamicin monoclonal antibody and Eu$^{3+}$ to successfully prepare a gentamicin antibody-labeled complex (Eu$^{3+}$-DTPA-GM-mAb).

Effect Detection

It was measured by gentamicin TRFIA, and specific steps were as follows:

a. coating: a coating antigen (GM-OVA) was diluted by CBS (0.05 mol·L$^{-1}$, pH=9.6) to a concentration of 4 μg·mL$^{-1}$, and coated on a 96-well plate with 100 μL per well, and incubated for 2 h at 37° C. in a constant temperature incubator, then the well plate was washed by a plate washing machine for 4 times, and pat-dried (the same below);

b. blocking: 300 μL 2% (m/v) skimmed milk prepared by PBS (0.01 mol·L$^{-1}$, pH=7.4) was added per well for incubation for 30 min at 37° C., then the well plate was washed for 4 times and pat-dried;

c. adding gentamicin standard samples and Eu$^{3+}$-DTPA-GM-mAb labels: gentamicin standard solution (namely, GM standard substances) having a concentration of the standard series were successively added to wells, 50 μL per well; then an europium-labeled antibody (Eu$^{3+}$-DTPA-GM-mAb) was diluted to 2 μg·mL$^{-1}$, and added to wells, 50 μL per well; after being oscillated for 30 s, the well plate was put to a 37° C. incubator for incubation for 1 h, and the plate was washed for 4 times and pat-dried;

d. adding an enhancement solution: 200 μL enhancement solution was added per well for oscillatory reaction for 10 min in dark place at 37° C.;

e. reading and analysis: values (CPS) of the fluorometer were read to establish a standard curve and calculate IC$_{50}$ values and IC$_{10}$ values.

Measured results of the olaquindox and gentamicin TRFIA were specifically shown in the table below:

TABLE 1

Measured results of time-resolved fluorescence immunoassay on different antibody labeled complexes

| Labeled complex | Binding ratio | CPS value Blank control value | 50% inhibition ratio | TRFIA detection sensitivity (ng/ml) IC$_{10}$ | IC$_{50}$ |
|---|---|---|---|---|---|
| Eu$^{3+}$-NOTA-OLA-mAb Example 1 | 23:1 | 33302179 | 16652471 | 0.18 | 3.54 |
| Eu$^{3+}$-EDTA-OLA-mAb Example 1 | 10:1 | 16126672 | 8062876 | 0.86 | 18.82 |
| Eu$^{3+}$-DTPA-OLA-mAb Example 2 | 8:1 | 14720951 | 7358998 | 1.13 | 22.96 |
| Eu$^{3+}$-NOTA-GM-mAb Example 2 | 19:1 | 30083374 | 15039198 | 0.32 | 6.98 |
| Eu$^{3+}$-EDTA-GM-mAb Example 3 | 7:1 | 13846826 | 6724019 | 2.48 | 37.61 |
| Eu$^{3+}$-EDTA-GM-mAb Example 4 | 9:1 | 15190072 | 7401391 | 1.08 | 21.52 |

It can be seen from Table 1 that compared with Comparative Examples 1-2, the olaquindox fluorescently-labeled antibody complex prepared in Example 1 of the present invention has a higher binding force, lower $IC_{10}$ and $IC_{50}$ detected by TRFIA; moreover, the fluorescently-labeled antibody complex prepared by using NOTA as a bifunctional chelating agent has a higher signal value CPS than that of the fluorescently-labeled antibody complex prepared by conventional DTPA and EDTA chelating agent derivatives. Similarly, compared with Comparative Examples 3-4, the gentamicin fluorescently-labeled antibody complex prepared in Example 2 has a higher binding force, lower $IC_{10}$ and $IC_{50}$ detected by TRFIA; moreover, the prepared fluorescently-labeled antibody complex has a higher signal value CPS than that of the fluorescently-labeled antibody complex prepared by conventional DTPA and EDTA chelating agent derivatives. Therefore, the results in Table 1 may indicate that the complex prepared by NOTA is stable, and has a high ion binding rate and strong fluorescence signal; and the established TRFIA immunoassay has a high detection sensitivity.

Second Embodiment

Example 1

A labeling method for improving signal intensity of time-resolved fluorescence, included the following steps: Preparation of an Olaquindox Antibody-Labeled Complex ($Eu^{3+}$-DOTA-OLA-mAb) was Set as an Example for Description:
(1) 6 mg of 2-S-(4-aminobenzene)-1,4,7,10 tetraazacyclononane-1,4,7,10-tetraacetic acid (p-$NH_2$-Bn-DOTA, abbreviated for DOTA) were weighed and dissolved into a 2 mL HEPES solution (0.01 mol·$L^{-1}$, pH=7.4) to be prepared into a DOTA chelating agent solution, where the solution was a solution A;
(2) 550 μL 20 mmol·L-1 glutaraldehyde solution was added to the solution A for reaction in dark place over the night at room temperature, where the solution was a solution B;
(3) 20 mg purified olaquindox monoclonal antibody lyophilized powder were weighed and dissolved into a 3 ml HEPES solution (0.01 mol·L-1, pH=7.4), and magnetic stirring was performed for mixing evenly at room temperature, thus obtaining a solution C;
in the example, the olaquindox monoclonal antibody (OLA-mAb) was prepared by a conventional method in the prior art (Reference: Yongyu Sang, and Renyao Jin, Development on Anti-Olaquindox Monoclonal Antibodies and Establishment of ELISA Method Thereof, Journal of Nuclear Agricultural Sciences, 2015, 29 (6):1081-1087). Ascitic fluid was purified by an octanoic acid-ammonium sulfate process, and then purified by passing a protein A affinity column, and lyophilized to obtain an OLA-mAb lyophilized powder.
(4) the solution B was dropwisely added to the solution C, then a pH value was adjusted to 9.0, and the mixed solution was stirred for reaction for 6 h in dark place at 4° C., thus obtaining a solution D;
(5) the solution D was loaded to a dialysis bag having a molecular weight cut-off of 8 KDa for dialysis by an HEPES solution (0.01 mol·L-1 pH=7.4), the solution was replaced for once every 4 h, and 4-5 times in total, then, a reaction solution in the dialysis bag was absorbed to obtain a solution E;
(6) 0.121 g $EuCl_3·6H_2O$ was weighed and prepared into a $EuCl_3$ solution having a concentration of 3.3×$10^{-2}$ mol·$L^{-1}$ with 10 mL ultrapure water, thus obtaining a solution F;
(7) 250 μL solution F was taken and added to the solution E for reaction for 4-6 h in dark place at room temperature, then the solution after reaction was placed to a dialysis bag having a molecular weight cut-off of 8 KDa, and the solution was replaced for once every 4 h during dialysis, and 4-5 times in total; the dialyzed solution was centrifuged for 3-5 times with a 30 KDa ultrafiltration centrifugal tube at 7000-9000 rpm, and the remaining solution was redissolved with a 5-10 ml HEPES solution (0.01 mol·$L^{-1}$, pH=7.4); where the prepared reaction solution was an olaquindox antibody complex immunolabelled by time-resolved fluorescence.

$Eu^{3+}$ content was measured by an Inductively Coupled Plasma-Atomic Emission Spectrometry (ICP-AES); a BCA protein concentration assay kit was used to measure the protein concentration in conjugates, then the protein concentration was converted into a molar concentration, and a binding ratio was calculated to 26:1, indicating a ratio of quantity; protein molecule: $Eu^{3+}$=1:26. The results indicated that the DOTA chelating agent was respectively bonded to olaquindox monoclonal antibody and $Eu^{3+}$ to successfully prepare an olaquindox antibody-labeled complex ($Eu^{3+}$-DOTA-OLA-mAb).

Effect Detection:
It was measured by olaquindox TRFIA, and specific steps were as follows:
a. coating: a coating antigen (OLA-HS-OVA) was diluted by CBS (0.05 mol·$L^{-1}$, pH=9.6) to a concentration of 5 μg·$mL^{-1}$, and coated on a 96-well plate with 100 μL per well, and incubated for 2 h at 37° C. in a constant temperature and humidity incubator, then the well plate was washed by a plate washing machine for 4 times, and pat-dried (the same below);
b. blocking: 300 μL 2% (m/v) skimmed milk prepared by PBS (0.01 mol·$L^{-1}$, pH=7.4) was added per well for incubation for 30 min at 37° C., then the well plate was washed for 4 times and pat-dried;
c. adding olaquindox standard samples and $Eu^{3+}$-DOTA-OLA-mAb labels: olaquindox standard solution having concentrations of the standard series were added to wells, 50 μL per well; then a europium-labeled antibody ($Eu^{3+}$-DOTA-OLA-mAb) was diluted to 2.5 μg·$mL^{-1}$, and added to wells, 50 μL per well; after being oscillated for 30 s, the well plate was put to a 37° C. incubator for incubation for 1 h, and the plate was washed for 4 times and pat-dried;
d. adding an enhancement solution: 200 μL enhancement solution was added per well for oscillatory reaction for 10 min in dark place at 37° C., and detected by a time-resolved fluorescence analyzer;
e. reading and analysis: values (CPS) of the fluorometer were read to establish a standard curve and calculate $IC_{50}$ values and $IC_{10}$ values.

Preparation of Various Reagents and Substances:
A. Olaquindox standard solution having concentrations of the standard series: the concentrations were successively 0 ng·mL-1, 0.01 ng·mL-1, 0.05 ng·mL-1, 0.1 ng·mL-1, 0.5 ng·$mL^{-1}$, 1.0 ng·$mL^{-1}$, 2.0 ng·$mL^{-1}$, 4.0 ng·$mL^{-1}$, 8.0 ng·$mL^{-1}$, 16.0 ng·$mL^{-1}$, and 32 ng·$mL^{-1}$, and obtained by diluting pure OLA; and the diluent was a 0.01 mol·L-1 phosphate buffer solution (pH=7.4) containing 5% (v/v) methanol.
B. Coating a buffer solution CBS: namely, a 0.05 mol·$L^{-1}$ carbonate buffer solution (pH=9.6); 1.49 g $Na_2CO_3$ and 2.93 g $NaHCO_3$ were weighed and adjusted to pH=9.6, and metered to a volume of 1000 mL with ultrapure water.

C. Blocking solution: namely, a 0.01 mol·L$^{-1}$ phosphate buffer solution (PBS) (pH=7.4) containing 2% (m/v, g/mL) skimmed milk powder.

D. Cleaning solution: namely, a 0.01 mol·L$^{-1}$ phosphate buffer solution (PBS) (pH=7.4) containing 0.05% (a volume fraction) Tween-20.

E. Diluent: namely, a 0.01 mol·L$^{-1}$ phosphate buffer solution (PBS) (pH=7.4) containing 5% (a volume fraction) methanol.

F. Enhancement solution: 120.0 mg a-thenoyltrifluoroacetone (TTA) and 386.6 mg trioctylphosphine oxide (TOPO) were accurately weighed and dissolved by adding 1.0 mL absolute ethyl alcohol, then 2.78 g potassium hydrogen phthalate and a small amount of deionized water were added, after dissolving at 40° C., 11.8 mL glacial acetic acid and 5 mL Triton X-100 were added, and finally metered to a volume of 2000 mL with water. The pH value was adjusted to 3.0, suction filtration was performed with degreasing cotton, and filtrate was standing over the night, and kept in dark place via a 4° C. refrigerator for further use.

G: Preparation of OLA-HS-OVA: a conventional method in the prior art was used for preparation available, and specifically as follows, 2.106 g olaquindox and 1.60 g succinic anhydride were accurately added to a three-necked round-bottom flask, and 80 mL pyridine was added for reflux reaction for 4 h at 115° C., the pyridine was removed by evaporation under reduced pressure, 60 mL icy distilled water was added to the remaining mixture, and a pH value was adjusted to 2.0-3.0 by 2 mol·L−1 HCl, then the remaining solution stayed over the night at 4° C. Afterwards, the remaining solution was subjected to suction filtration under reduced pressure, and washed by icy distilled water for 3 times, and dried by suction, and the obtained substance was OLA-HS;

14.5 mg OLA-HS were weighed and dissolved into 0.8 ml DMF, and 4.6 mg NHS and 8.2 mg DCC were added for stirring reaction for 10 h in dark place at room temperature. The reaction solution was centrifuged (2000 rpm, 10 min), precipitate was discarded and supernate was a reaction solution a.

20 mg OVA were weighed and dissolved into a 5 ml phosphate buffer solution (PBS, 0.01 mol·L$^{-1}$, PH=7.4) to obtain a reaction solution b. The reaction solution b was put on a magnetic stirrer; 0.6 ml reaction solution a was slowly added to the reaction solution b dropwisely at 4° C., and stirred for reaction over the night at 4° C. In the following day, the reaction solution was put to a dialysis bag for dialysis for 4-5 times per day with a phosphate buffer solution (0.01 mol·L$^{-1}$, pH=7.4), then dialyzed for 12 h by ultrapure water, and centrifuged; precipitate was discarded and supernate was subpackaged to obtain OLA-HS-OVA, and OLA-HS-OVA was kept at −20° C. for further use.

Example 2

A labeling method for improving signal intensity of time-resolved fluorescence, included the following steps: Preparation of a Gentamicin Antibody-Labeled Complex (Eu$^{3+}$-DOTA-GM-mAb) was Set as an Example for Description:

(1) 6 mg 2-S-(4-aminobenzene)-1,4,7,10 tetraazacyclononane-1,4,7,10-tetraacetic acid (p-NH$_2$-Bn-DOTA, abbreviated for DOTA) were weighed and dissolved into a 2 mL HEPES solution (0.01 mol·L$^{-1}$, pH=7.4) to be prepared into a DOTA chelating agent solution, where the solution was a solution A;

(2) 550 μL 20 mmol·L$^{-1}$ glutaraldehyde solution was added to the solution A for reaction in dark place over the night at room temperature, where the solution was a solution B;

(3) 20 mg purified GM-mAb lyophilized powder were weighed and dissolved into a 3 ml HEPES solution (0.01 mol·L$^{-1}$, pH=7.4), and magnetic stirring was performed for mixing evenly at room temperature, thus obtaining a solution C;

GM-mAb was prepared by a conventional method in the prior art (Reference: Renyao Jin, and Jianxiang Wu; Development on Gentamicin Monoclonal Antibodies and Establishment of ELISA Method Thereof, Journal of Nuclear Agricultural Sciences, 2013, 27 (1):88-92). After ascitic fluid was prepared, and roughly purified by octanoic acid-ammonium sulfate, and then purified by a Protein A affinity column, and lyophilized to obtain a GM-mAb lyophilized powder.

(4) the solution B was dropwisely added to the solution C, then a pH value was adjusted to 9.0, and the mixed solution was stirred for reaction for 4-6 h in dark place at 4° C., thus obtaining a solution D;

(5) the solution D was loaded to a dialysis bag having a molecular weight cut-off of 8 KDa for dialysis by an HEPES solution (0.01 mol·L$^{-1}$, pH=7.4), the solution was replaced for once every 4 h, and 5 times in total, then, a reaction solution in the dialysis bag was absorbed to obtain a solution E;

(6) 0.121 g EuCl$_3$.6H$_2$O was weighed and prepared into a EuCl$_3$ solution having a concentration of $3.3 \times 10^{-2}$ mol·L$^{-1}$ with 10 mL ultrapure water, thus obtaining a solution F;

(7) 250 μL solution F was taken and added to the solution E for reaction for 4-6 h in dark place at room temperature, then the solution after reaction was placed to a dialysis bag having a molecular weight cut-off of 8 KDa for dialysis by an HEPES (0.01 mol·L$^{-1}$, pH=7.4) solution; and the solution was replaced for once every 4 h during dialysis, and 4-5 times in total; the dialyzed solution was centrifuged for 3-5 times with a 30 KDa ultrafiltration centrifugal tube at 7000-9000 rpm, and the remaining solution was redissolved with a 5-10 ml HEPES solution (0.01 mol·L$^{-1}$, pH=7.4); where the prepared reaction solution was a gentamicin antibody-labeled complex.

Eu$^{3+}$ content was measured by an Inductively Coupled Plasma-Atomic Emission Spectrometry (ICP-AES); a BCA protein concentration assay kit was used to measure the protein concentration in conjugates, then the protein concentration was converted into a molar concentration, and a binding ratio was calculated to 21:1, indicating a ratio of quantity; protein molecule: Eu$^{3+}$=1:21. The results indicated that the DOTA chelating agent was respectively bonded to gentamicin monoclonal antibody and Eu$^{3+}$ to successfully prepare a gentamicin antibody-labeled complex (Eu$^{3+}$-DOTA-GM-mAb).

Effect Detection:

It was measured by gentamicin TRFIA, and specific steps were as follows:

a. coating: a coating antigen (GM-OVA) was diluted by CBS (0.05 mol·L$^{-1}$, pH=9.6) to a concentration of 4 μg·mL$^{-1}$, and coated on a 96-well plate with 100 μL per well, and incubated for 2 h at 37° C. in a constant temperature and humidity incubator, then the well plate was washed by a plate washing machine for 4 times, and pat-dried (the same below);

b. blocking: 300 μL 2% (m/v) skimmed milk prepared by PBS (0.01 mol·L$^{-1}$, pH=7.4) was added per well for incubation for 30 min at 37° C., then the well plate was washed for 4 times and pat-dried;

c. adding gentamicin standard samples and Eu$^{3+}$-DOTA-GM-mAb labels: gentamicin standard solution having concentrations of the standard series were added to wells, 50 μL per well; then an europium-labeled antibody (Eu$^{3+}$-DOTA-GM-mAb) was diluted to 2 μg·mL$^{-1}$, and added to wells, 50 μL per well; after being oscillated for 30 s, the well plate was put to a 37° C. incubator for incubation for 1 h, and the plate was washed for 4 times and pat-dried;

d. adding an enhancement solution: 200 μL enhancement solution was added per well for oscillatory reaction for 10 min in dark place at 37° C.

e. reading and analysis: values (CPS) of the fluorometer were read to establish a standard curve and calculate IC$_{50}$ values and IC$_{10}$ values.

Preparation of Various Reagents:

A. Gentamicin standard solution having concentrations of the standard series: the concentrations were successively 0 ng·mL$^{-1}$, 1 ng·mL$^{-1}$, 2 ng·mL$^{-1}$, 4 ng·mL$^{-1}$, 0.5 ng·mL$^{-1}$, 8 ng·mL$^{-1}$, 16 ng·mL$^{-1}$, 32 ng·mL$^{-1}$, 64 ng·mL$^{-1}$, 128 ng·mL$^{-1}$, and obtained by diluting pure gentamicin; and the diluent is a 0.01 mol·L$^{-1}$ phosphate buffer solution (pH=7.4).

B. Coating a buffer solution: namely, a 0.05 mol·L$^{-1}$ carbonate buffer solution (pH=9.6); 1.49 g Na$_2$CO$_3$ and 2.93 g NaHCO$_3$ were weighed and adjusted to pH=9.6, and metered to a volume of 1000 mL with ultrapure water.

C. Blocking solution: namely, a 0.01 mol·L$^{-1}$ phosphate buffer solution (PBS) (pH=7.4) containing 2% (m/v, g·mL$^{-1}$) skimmed milk powder.

D. Cleaning solution: namely, a 0.01 mol·L$^{-1}$ phosphate buffer solution (PBS) (pH=7.4) containing 0.05% (a volume fraction) Tween-20.

E. Diluent: namely, a 0.01 mol·L$^{-1}$ phosphate buffer solution (PBS) (pH=7.4).

F. Enhancement solution: 120.0 mg a-thenoyltrifluoroacetone (TTA) and 386.6 mg trioctylphosphine oxide (TOPO) were accurately weighed and dissolved by adding 1.0 mL absolute ethyl alcohol, then 2.78 g potassium hydrogen phthalate and a small amount of deionized water were added, after dissolving at 40° C., 11.8 mL glacial acetic acid and 5 mL Triton X-100 were added, and finally metered to a volume of 2000 mL with water. The pH value was adjusted to 3.0, suction filtration was performed with degreasing cotton, and filtrate was standing over the night, and kept in dark place via a 4° C. refrigerator for further use.

G: Synthesis of GM-OVA: a conventional method in the prior art was used for preparation available, and specifically as follows, 20 mg GM and 12 mg OVA were taken, and respectively dissolved by 1 ml ultrapure water; then GM solution was dropwisely added to OVA solution while stirring slowly; 62 mg carbodiimide (EDC) were weighed and dissolved into 1 ml ultrapure water, then the above mixed solution was added dropwisely, and stirred for reaction for 4 h at room temperature; afterwards, the reaction product was loaded to a dialysis bag for dialysis for 2 d, and the solution was replaced for once every 4 h, after replacing for 4-5 times, the remaining solution was subpackaged, and kept at −20° C.

Comparative Example 1

Preparation of an Olaquindox Antibody-Labeled Complex (Eu$^{3+}$-EDTA-OLA-mAb):

(1) 7 mg Aminobenzy-EDTA (hereinafter referred to as EDTA) were weighed and dissolved into a 2 mL HEPES solution (0.01 mol·L$^{-1}$, pH=7.4) to be prepared into an EDTA chelating agent solution, where the solution was a solution A;

(2) 550 μL 20 mmol·L$^{-1}$ glutaraldehyde solution was added to the solution A for reaction in dark place over the night at room temperature, where the solution was a solution B;

(3) 20 mg purified OLA-mAb lyophilized powder were weighed and dissolved into a 3 ml HEPES solution (0.01 mol·L$^{-1}$, pH=7.4), and magnetic stirring was performed for mixing evenly at room temperature, thus obtaining a solution C;

(4) the solution B was dropwisely added to the solution C, then a pH value was adjusted to 9.0, and the mixed solution was stirred for reaction for 4-6 h in dark place at 4° C., thus obtaining a solution D;

(5) the solution D was loaded to a dialysis bag having a molecular weight cut-off of 8 KDa for dialysis by an HEPES solution (0.01 mol·L$^{-1}$, pH=7.4), the solution was replaced for once every 4 h, and 4-5 times in total, then, a reaction solution in the dialysis bag was absorbed to obtain a solution E;

(6) 0.121 g EuCl$_3$·6H$_2$O was weighed and prepared into a EuCl$_3$ solution having a concentration of $3.3\times10^{-2}$ mol·L$^{-1}$ with 10 mL ultrapure water, thus obtaining a solution F;

(7) 250 μL solution F was taken and added to the solution E for reaction for 4-6 h in dark place at room temperature, then the solution after reaction was placed to a dialysis bag having a molecular weight cut-off of 8000 Da for dialysis by an HEPES (0.01 mol·L$^{-1}$, pH=7.4), and the solution was replaced for once every 4 h during dialysis, and 4-5 times in total; the dialyzed solution was centrifuged for 3-5 times with a 30 KDa ultrafiltration centrifugal tube at 7000-9000 rpm, and the remaining solution was redissolved with a 5-10 ml HEPES solution (0.01 mol·L$^{-1}$, pH=7.4); where the prepared reaction solution was an olaquindox antibody complex immunolabelled by time-resolved fluorescence.

Eu$^{3+}$ content was measured by an Inductively Coupled Plasma-Atomic Emission Spectrometry (ICP-AES); a BCA protein concentration assay kit was used to measure the protein concentration in conjugates, then the protein concentration was converted into a molar concentration, and a binding ratio was calculated to 11:1, indicating a ratio of quantity; protein molecule: Eu$^{3+}$=1:11. The results indicated that EDTA was respectively bonded to olaquindox monoclonal antibody and Eu$^{3+}$ to successfully prepare an olaquindox antibody-labeled complex.

Effect Detection:

It was measured by olaquindox TRFIA, and specific steps were as follows:

a. coating: a coating antigen (OLA-HS-OVA) was diluted by CBS (0.05 mol·L$^{-1}$, pH=9.6) to a concentration of 5 μg·mL$^{-1}$, and coated on a 96-well plate with 100 μL per well, and incubated for 2 h at 37° C. in a constant temperature and humidity incubator, then the well plate was washed by a plate washing machine for 4 times, and pat-dried (the same below);

b. blocking: 300 μL 2% skimmed milk prepared by PBS (0.01 mol·L$^{-1}$, pH=7.4) was added per well for incubation for 30 min at 37° C., then the well plate was washed and pat-dried;
c. adding olaquindox standard samples and Eu$^{3+}$-EDTA-OLA-mAb labels: OLA standard solution having concentrations of the standard series was added to wells, 50 μL per well; then an europium-labeled antibody (Eu$^{3+}$-EDTA-OLA-mAb) was diluted to 2.5 μg·mL$^{-1}$, and added to wells, 50 μL per well; after being oscillated for 30 s, the well plate was put to a 37° C. incubator for incubation for 1 h, and the plate was washed and pat-dried;
d. adding an enhancement solution: 200 μL enhancement solution was added per well for oscillatory reaction for 10 min in dark place at 37° C.
e. reading and analysis: values (CPS) of the fluorometer were read to establish a standard curve and calculate IC$_{50}$ values and IC$_{10}$ values.

Comparative Example 2

Preparation of an Olaquindox Antibody-Labeled Complex (Eu$^{3+}$-DTPA-OLA-mAb):
(1) 7 mg p-NH$_2$-Bn-DTPA (hereinafter referred to as DTPA) were weighed and dissolved into a 2 ml HEPES buffer solution (0.01 mol·L$^{-1}$, pH=7.4) to be prepared into a DTPA chelating agent solution, where the reaction solution was a solution A;
(2) 550 μL 20 mmol·L$^{-1}$ glutaraldehyde solution was added to the solution A for reaction in dark place over the night at room temperature, where the solution was a solution B;
(3) 20 mg purified OLAmAb lyophilized powder were weighed and dissolved into a 3 ml HEPES solution (0.01 mol·L$^{-1}$, pH=7.4), and magnetic stirring was performed for mixing evenly at room temperature, thus obtaining a solution C; and the preparation method and concentration of the OLA-mAb solution were the same as those in Example 1;
the solution B was dropwisely added to the solution C, then a pH value was adjusted to 9.0 by NaOH, and the mixed solution was stirred for reaction for 4-6 h in dark place at 4° C., thus obtaining a solution D;
(4) the solution D was loaded to a dialysis bag having a molecular weight cut-off of 8 KDa for dialysis by an HEPES solution (0.01 mol·L$^{-1}$, pH=7.4), the solution was replaced for once every 4 h, and 4-5 times in total, after replacing for 5-6 times, a reaction solution in the dialysis bag was absorbed to obtain a solution E;
(5) 0.121 g EuCl$_3$.6H$_2$O was weighed and prepared into a EuCl$_3$ solution having a concentration of 3.3×10$^{-2}$ mol·L$^{-1}$ with 10 mL ultrapure water, thus obtaining a solution F;
(6) 250 μL solution F was taken and added to the solution E for reaction for 4-6 h in dark place at room temperature, then the solution after reaction was placed to a dialysis bag having a molecular weight cut-off of 8 KDa for dialysis by an HEPES (0.01 mol·L$^{-1}$, pH=7.4), and the solution was replaced for once every 4 h during dialysis, and 4-5 times in total; the dialyzed solution was centrifuged for 3-5 times with a 30 KDa ultrafiltration centrifugal tube at 7000-9000 rpm, and the remaining solution was redissolved with a 5-10 ml HEPES solution (0.01 mol·L$^{-1}$, pH=7.4); where the prepared reaction solution was an olaquindox antibody complex immunolabelled by time-resolved fluorescence.

Eu$^{3+}$ content was measured by an Inductively Coupled Plasma-Atomic Emission Spectrometry (ICP-AES); a BCA protein concentration assay kit was used to measure the protein concentration in conjugates, then the protein concentration was converted into a molar concentration, and a binding ratio was calculated to 9:1, indicating a ratio of quantity; protein molecule: Eu$^{3+}$=1:9. The results indicated that DTPA was respectively bonded to olaquindox monoclonal antibody and Eu$^{3+}$ to successfully prepare an olaquindox antibody-labeled complex (Eu$^{3+}$-DTPA-OLA-mAb).

Effect Detection:
It was measured by olaquindox TRFIA, and specific steps were as follows:
a. coating: a coating antigen (OLA-HS-OVA) was diluted by CBS (0.05 mol·L$^{-1}$, pH=9.6) to a concentration of 5 μg·mL$^{-1}$, and coated on a 96-well plate with 100 μL per well, and incubated for 2 h at 37° C. in a constant temperature and humidity incubator, then the well plate was washed by a plate washing machine for 4 times, and pat-dried (the same below);
b. blocking: 300 μL 2% (m/v) skimmed milk prepared by PBS (0.01 mol·L$^{-1}$, pH=7.4) was added per well for incubation for 30 min at 37° C., then the well plate was washed for 4 times and pat-dried;
c. adding olaquindox standard samples and Eu$^{3+}$-EDTA-OLA-mAb labels: OLA standard solution having concentrations of the standard series was added to wells, 50 μL per well; then an europium-labeled antibody (Eu$^{3+}$-DTPA-OLA-mAb) was diluted to 2.5 μg·mL$^{-1}$, and added to wells, 50 μL per well; after being oscillated for 30 s, the well plate was put to a 37° C. incubator for incubation for 1 h, and the plate was washed for 4 times and pat-dried;
d. adding an enhancement solution: 200 μL enhancement solution was added per well for oscillatory reaction for 10 min in dark place at 37° C., and detected by a time-resolved fluorescence analyzer;
e. reading and analysis: values (CPS) of the fluorometer were read to establish a standard curve and calculate IC$_{50}$ values and IC$_{10}$ values.

Comparative Example 3

Preparation of a Gentamicin Antibody-Labeled Complex (Eu$^{3+}$-EDTA-GM-mAb):
(1) 7 mg Aminobenzy-EDTA (hereinafter referred to as EDTA) were weighed and dissolved into a 2 mL HEPES solution (0.01 mol·L$^{-1}$, pH=7.4) to be prepared into an EDTA chelating agent solution, where the solution was a solution A;
(2) 550 μL 20 mmol·L$^{-1}$ glutaraldehyde solution was added to the solution A for reaction in dark place over the night at room temperature, where the solution was a solution B;
(3) 20 mg purified GM-mAb lyophilized powder were weighed and dissolved into a 3 ml HEPES solution (0.01 mol·L$^{-1}$, pH=7.4), and magnetic stirring was performed for mixing evenly at room temperature, thus obtaining a solution C; and the preparation method and concentration of the GM-mAb solution were the same as those in Example 2;
(4) the solution B was dropwisely added to the solution C, then a pH value was adjusted to 9.0, and the mixed solution was stirred for reaction for 4-6 h in dark place at 4° C., thus obtaining a solution D;

(5) the solution D was loaded to a dialysis bag having a molecular weight cut-off of 8 KDa for dialysis by an HEPES solution (0.01 mol·L$^{-1}$, pH=7.4), after the solution was replaced for 5-6 times, a reaction solution in the dialysis bag was absorbed to obtain a solution E;

(6) 0.121 g EuCl$_3$.6H$_2$O was weighed and prepared into a EuCl$_3$ solution having a concentration of $3.3 \times 10^{-2}$ mol·L$^{-1}$ with 10 mL ultrapure water, thus obtaining a solution F;

(7) 250 μL solution F was taken and added to the solution E for reaction for 4-6 h in dark place at room temperature, then the solution after reaction was placed to a dialysis bag having a molecular weight cut-off of 8 KDa for dialysis by an HEPES (0.01 mol·L$^{-1}$, pH=7.4) solution; and the solution was replaced for once every 4 h during dialysis, and 4-5 times in total; the dialyzed solution was centrifuged for 3-5 times with a 30 KDa ultrafiltration centrifugal tube at 7000-9000 rpm, and the remaining solution was redissolved with a 5-10 ml HEPES solution (0.01 mol·L$^{-1}$, pH=7.4); where the prepared reaction solution was a gentamicin antibody-labeled complex.

Eu$^{3+}$ content was measured by an Inductively Coupled Plasma-Atomic Emission Spectrometry (ICP-AES); a BCA protein concentration assay kit was used to measure the protein concentration in conjugates, then the protein concentration was converted into a molar concentration, and a binding ratio was calculated to 8:1, indicating a ratio of quantity; protein molecule: Eu$^{3+}$=1:8. The results indicated that EDTA was respectively bonded to gentamicin monoclonal antibody and Eu$^{3+}$ to successfully prepare a gentamicin antibody-labeled complex (Eu$^{3+}$-EDTA-GM-mAb).

Effect Detection:

It was measured by gentamicin TRFIA, and specific steps were as follows:

a. coating: a coating antigen (GM-OVA) was diluted by CBS (0.05 mol·L$^{-1}$, pH=9.6) to a concentration of 4 μg·mL$^{-1}$, and coated on a 96-well plate with 100 μL per well, and incubated for 2 h at 37° C. in a constant temperature and humidity incubator, then the well plate was washed by a plate washing machine for 4 times, and pat-dried (the same below);

b. blocking: 300 μL 2% (m/v) skimmed milk prepared by PBS (0.01 mol·L$^{-1}$, pH=7.4) was added per well for incubation for 30 min at 37° C., then the well plate was washed for 4 times and pat-dried;

c. adding gentamicin standard samples and Eu$^{3+}$-EDTA-GM-mAb labels: gentamicin standard solution having concentrations of the standard series were added to wells, 50 μL per well; then an europium-labeled antibody (Eu$^{3+}$-EDTA-GM-mAb) was diluted to 2 μg·mL$^{-1}$, and added to wells, 50 μL per well; after being oscillated for 30 s, the well plate was put to a 37° C. incubator for incubation for 1 h, and the plate was washed for 4 times and pat-dried;

d. adding an enhancement solution: 200 μL enhancement solution was added per well for oscillatory reaction for 10 min in dark place at 37° C.

e. reading and analysis: values (CPS) of the fluorometer were read to establish a standard curve and calculate IC$_{50}$ values and IC$_{10}$ values.

Comparative Example 4

Preparation of a Gentamicin Antibody-Labeled Complex (Eu$^{3+}$-DTPA-GM-mAb):

(1) 7 mg p-NH$_2$-Bn-DTPA were weighed and dissolved into a 2 ml HEPES buffer solution (0.01 mol·L$^{-1}$, pH=7.4) to be prepared into a DTPA chelating agent solution, where the reaction solution was a solution A;

(2) 550 μL 20 mmol·L$^{-1}$ glutaraldehyde solution was added to the solution A for reaction in dark place over the night at room temperature, where the solution was a solution B;

(3) 20 mg purified GM-mAb lyophilized powder were weighed and dissolved into a 3 ml HEPES solution (0.01 mol·L$^{-1}$, pH=7.4), and magnetic stirring was performed for mixing evenly at room temperature, thus obtaining a solution C; and the preparation method and concentration of the GM-mAb solution were the same as those in Example 2;

(4) the solution A and B were dropwisely added to the solution C, then a pH value was adjusted to 9.0 by NaOH, and the mixed solution was stirred for reaction for 4-6 h in dark place at 4° C., thus obtaining a solution D;

(5) the solution D was loaded to a dialysis bag having a molecular weight cut-off of 8 KDa for dialysis by an HEPES solution (0.01 mol·L$^{-1}$, pH=7.4), after the solution was replaced for 5-6 times, a reaction solution in the dialysis bag was absorbed to obtain a solution E;

(6) 0.121 g EuCl$_3$.6H$_2$O was weighed and prepared into a EuCl$_3$ solution having a concentration of $3.3 \times 10^{-2}$ mol·L$^{-1}$ with 10 mL ultrapure water, thus obtaining a solution F;

(7) 250 μL solution F was taken and added to the solution E for reaction for 4-6 h in dark place at room temperature, then the solution after reaction was placed to a dialysis bag having a molecular weight cut-off of 8 KDa for dialysis by an HEPES (0.01 mol·L$^{-1}$, pH=7.4) solution; and the solution was replaced for once every 4 h during dialysis, and 4-5 times in total; the dialyzed solution was centrifuged for 3-5 times with a 30 KDa ultrafiltration centrifugal tube at 7000-9000 rpm, and the remaining solution was redissolved with a 5-10 ml HEPES solution (0.01 mol·L$^{-1}$, pH=7.4); where the prepared reaction solution was a gentamicin antibody-labeled complex.

Eu$^{3+}$ content was measured by an Inductively Coupled Plasma-Atomic Emission Spectrometry (ICP-AES); a BCA protein concentration assay kit was used to measure the protein concentration in conjugates, then the protein concentration was converted into a molar concentration, and a binding ratio was calculated to 10:1, indicating a ratio of quantity; protein molecule: Eu$^{3+}$=1:10. The results indicated that EDTA was respectively bonded to gentamicin monoclonal antibody and Eu$^{3+}$ to successfully prepare a gentamicin antibody-labeled complex (Eu$^{3+}$-DTPA-GM-mAb).

Effect Detection:

It was measured by gentamicin TRFIA, and specific steps were as follows:

a. coating: a coating antigen (GM-OVA) was diluted by CBS (0.05 mol·L$^{-1}$, pH=9.6) to a concentration of 4 μg·mL$^{-1}$, and coated on a 96-well plate with 100 μL per well, and incubated for 2 h at 37° C. in a constant temperature and humidity incubator, then the well plate was washed by a plate washing machine for 4 times, and pat-dried (the same below);

b. blocking: 300 μL 2% (m/v) skimmed milk prepared by PBS (0.01 mol·L$^{-1}$, pH=7.4) was added per well for incubation for 30 min at 37° C., then the well plate was washed for 4 times and pat-dried;

c. adding gentamicin standard samples and Eu$^{3+}$-DTPA-GM-mAb labels: gentamicin standard solution (namely, GM standard substances) having concentrations of the standard series were added to wells, 50 μL per well; then an europium-labeled antibody (Eu$^{3+}$-DTPA-GM-mAb) was diluted to 2 μg·mL$^{-1}$, and added to wells, 50 μL per well; after being oscillated for 30 s, the well plate was put to a 37° C. incubator for incubation for 1 h, and the plate was washed for 4 times and pat-dried;

d. adding an enhancement solution: 200 μL enhancement solution was added per well for oscillatory reaction for 10 min in dark place at 37° C.

e. reading and analysis: values (CPS) of the fluorometer were read to establish a standard curve and calculate IC$_{50}$ values and IC$_{10}$ values.

Measured results of the olaquindox and gentamicin TR-FIA were specifically shown in the table below:

TABLE 2

Measured results of time-resolved fluorescence immunoassay on different antibody labeled complexes

| Fluorescent antibody complex | Binding ratio | Blank control value | 50% inhibition ratio | TRFIA detection sensitivity (ng/ml) IC$_{10}$ | IC$_{50}$ |
|---|---|---|---|---|---|
| Eu$^{3+}$-DOTA-OLA-mAb Example 1 | 26:1 | 35793201 | 17916923 | 0.12 | 2.86 |
| Eu$^{3+}$-EDTA-OLA-mAb Example 1 | 11:1 | 16493247 | 8239667 | 0.87 | 19.62 |
| Eu$^{3+}$-DTPA-OLA-mAb Example 2 | 9:1 | 15423504 | 7712513 | 1.44 | 24.73 |
| Eu$^{3+}$-DOTA-GM-mAb Example 2 | 21:1 | 31074439 | 15507132 | 0.26 | 6.08 |
| Eu$^{3+}$-EDTA-GM-mAb Example 3 | 8:1 | 15228128 | 7518224 | 1.92 | 35.65 |
| Eu$^{3+}$-DTPA-GM-mAb Example 4 | 10:1 | 15711612 | 7850608 | 0.96 | 20.45 |

It can be seen from Table 2 that compared with Comparative Examples 1-2, the olaquindox fluorescent antibody complex prepared in Example 1 of the present invention has a higher binding force, a more stable structure, lower IC$_{10}$ and IC$_{50}$; moreover, the fluorescently-labeled antibody complex prepared by using DOTA as a bifunctional chelating agent has a higher signal value CPS than that of the fluorescently-labeled antibody complex prepared by conventional DTPA and EDTA chelating agent derivatives.

Similarly, compared with Comparative Examples 3-4, the gentamicin fluorescent antibody complex prepared in Example 2 has a maximum higher binding force, the sensitivity of the detection analysis was optimal, and the signal intensity was maximum. To sum up, it may indicate that the complex prepared by using DOTA as a bifunctional chelating agent is stable, and has a high ion binding rate and strong fluorescence signal; the established TRFIA immunoassay has a high detection sensitivity.

A person skilled in the art should understand that each technical feature of the above examples may be in any combination; to achieve brief description, all the possible combinations of each technical feature of the above examples are not described one by one. But as long as the combinations of these technical features are not contradictory, the combinations should be regarded to fall within the scope of the description.

The invention claimed is:

1. A labeling method for improving signal intensity of time-resolved fluorescence, comprising the following steps:

weighing and dissolving 4-7 mg of 2-S-(4-aminobenzene)-1,4,7 triazacyclononane-1,4,7-triacetic acid (NOTA) into 1 mL of a 4-hydroxyethylpiperazine ethanesulfonic acid (HEPES) solution at pH 7.4 with a concentration of 0.01 mol·L$^{-1}$ to obtain an NOTA chelating agent solution, wherein the NOTA chelating agent solution is a first solution;

adding 500-700 μL of a glutaraldehyde solution with a concentration of 20 mmol·L$^{-1}$ to the first solution for reaction in dark place over a night at room temperature to obtain a second solution;

weighing and dissolving 20-30 mg of purified lyophilized powder of a monoclonal antibody into 3 ml of the HEPES solution at pH 7.4 with the concentration of 0.01 mol·L$^{-1}$, and performing magnetic stirring for mixing evenly at room temperature, thus to obtain a third solution;

dropwisely adding the second solution to the third solution, then adjusting a pH value to 9.0, and stirring the mixed second and third solutions for reaction for 4-6 h in dark place at 4° C., thus to obtain a fourth solution;

loading the fourth solution to a dialysis bag having a molecular weight cut-off of 8 KDa for dialysis by the HEPES solution at pH 7.4 with the concentration of 0.01 mol·L$^{-1}$, replacing the HEPES solution once every 4 h and replacing 4-6 times in total, and then absorbing a reaction solution in the dialysis bag to obtain a fifth solution;

weighing 0.11-0.15 g of EuCl$_3$·6H$_2$O and preparing a EuCl$_3$ solution with 10 mL of ultrapure water, thus to obtaining a sixth solution; and taking and adding 200-400 μL of the sixth solution to the fifth solution for reaction for 4-6 h in dark place at room temperature, then placing the mixed fifth and sixth solution after reaction to another dialysis bag having a molecular weight cut-off of 8 KDa for dialysis, and replacing the HEPES solution once every 4 h and 4-5 times in total; centrifuging the dialyzed solution for 3-5 times with a 30 KDa ultrafiltration centrifugal tube at 7000-9000 rpm, and redissolving a remaining solution with 5-10 ml of the HEPES solution at pH 7.4 with the concentration of 0.01 mol·L$^{-1}$; wherein the obtained reaction solution is an olaquindox antibody complex immunolabelled by time-resolved fluorescence.

2. The labeling method for improving signal intensity of time-resolved fluorescence according to claim 1, wherein the monoclonal antibody is an olaquindox monoclonal antibody or a gentamicin monoclonal antibody.

* * * * *